(12) United States Patent
Price, Jr.

(10) Patent No.: US 6,991,657 B1
(45) Date of Patent: Jan. 31, 2006

(54) ADJUSTABLE PROSTHETIC SOCKET

(75) Inventor: James B. Price, Jr., 8478 Rocky River Rd., Harrisburg, NC (US) 28075

(73) Assignee: James B. Price, Jr., Harrisburg, NC (US)

(*) Notice: Subject to any disclaimer, the term of this patent is extended or adjusted under 35 U.S.C. 154(b) by 0 days.

(21) Appl. No.: 10/887,401

(22) Filed: Jul. 8, 2004

(51) Int. Cl.
*A61F 2/60* (2006.01)
*A61F 2/78* (2006.01)

(52) U.S. Cl. ........................................................ 623/33
(58) Field of Classification Search .................. 623/27, 623/32–38
See application file for complete search history.

(56) References Cited

U.S. PATENT DOCUMENTS

| 4,842,608 | A | * | 6/1989 | Marx et al. | ................... 623/33 |
| 4,872,879 | A | | 10/1989 | Shamp | |
| 4,988,360 | A | | 1/1991 | Shamp | |
| 5,529,575 | A | * | 6/1996 | Klotz | .......................... 623/33 |
| 5,653,766 | A | | 8/1997 | Naser | |
| 5,728,165 | A | * | 3/1998 | Brown, Sr. | .................. 623/33 |

* cited by examiner

*Primary Examiner*—Bruce E. Snow
(74) *Attorney, Agent, or Firm*—Hammer, Ashburg &Hanf, P.C.

(57) ABSTRACT

The instant invention is an adjustable prosthetic socket. The adjustable prosthetic socket of the instant invention includes a cup, a lateral wall, and a brim. The cup includes a lateral cutaway portion, a lower closed portion, and an upper open portion. The brim is adapted for adjustable mounting in said cup via said upper open portion while the lateral wall is adapted for adjustable mounting in said lateral cutaway.

19 Claims, 10 Drawing Sheets

ADJUSTABLE PROSTHETIC SOCKET

FIELD OF INVENTION

The instant invention relates to an adjustable prosthetic socket.

BACKGROUND OF THE INVENTION

Advances with prostheses, e.g. transfemoral prostheses, in recent years have enabled individuals with amputated extremities to pursue a reasonably normal life, and the use of such prostheses is generally well known. Peripheral vascular disease (poor circulation of the blood), cancer, diabetes, accidents, and congenital disorders are the major causes of amputation. Amputations in the case of various diseases are often performed as a lifesaving measure.

The use of transfemoral prostheses by transfemoral amputees is generally well known. In general, transfemoral prostheses include the following four major components: a socket, a knee system, a shank, and a foot-ankle system. A variety of sockets, knee systems, shanks, and foot systems are available, and can be combined to produce a transfemoral prosthesis that best meets the need of each individual transfemoral amputee. The socket is the interface between the amputee and the prosthesis, and it provides the means for transferring the weight of the amputee to the ground by the way of the prosthesis. The knee system provides a transfemoral amputee a normal appearance while walking. The primary purpose of the shank is to transfer the vertical loads caused by the weight of the amputee to the foot system, and subsequently to the ground.

The use of a quadrilateral socket ("quad socket") for fitting a transfemoral prosthesis to the residual limb ("residuum") of a transfemoral amputee is generally well known. In general, a quad socket has four walls (quad), and each wall has a specific function. The four walls of a quad socket include an anterior wall, a posterior wall, a medial wall, and a lateral wall.

Several factors should be considered in order to achieve a proper design for a socket including the following: whether the socket satisfactory transmits the load; whether the socket provides satisfactory stability; whether the socket provides efficient control for mobility; whether the socket is easily fitted; and whether the socket is comfortable.

U.S. Pat. No. 4,872,879 discloses an ischial containment socket for securing an artificial limb to the residual thigh of an above-knee amputee. The ischial containment socket includes an interface to which a cup shape frame can be selectively secured, and the interface has open proximal and distal ends. Furthermore, said interface includes a posterior, a medial, a lateral, and an anterior wall. The medial wall includes an extension, which overlaps the anterior wall. The overlapping relation of the extension and the anterior wall forms a peripheral discontinuity, which permits the peripheral dimensions of said interface to be adjusted by sliding the contiguously juxtaposed, and overlapping extension and the anterior wall. The proximal portion of both the posterior and medial walls terminate in a containment brim.

U.S. Pat. No. 4,988,360 discloses a method for fitting the interface portion of an ischial containment socket to the residual limb of above-knee amputee. The interface-fitting module includes a sleeve-like body portion with open proximal and distal ends, and a frame. Said sleeve-like body includes a posterior, a medial, a lateral, and an anterior wall. The lateral wall includes an extension, which overlaps the anterior wall, and the overlapping relation of the extension and the anterior wall forms a peripheral discontinuity, which permits the peripheral dimensions of said interface to be adjusted by sliding the contiguously juxtaposed, and overlapping extension and the anterior wall. The sleeve-like body portion is further provided with a brim.

U.S. Pat. No. 5,653,766 discloses a prosthetic device for use immediately after a limb reduction surgery until the patient is fitted with a more permanent prosthesis. The post prosthetic device includes a sleeve that is at least partially received about a limb. The sleeve includes a first portion and a second portion. The first portion includes a longitudinal slit, which enables the inner surface circumference of the first portion to be adjusted.

Despite the advances in the art, there is still a need for an improved socket, which is easily fitted, and provides a high level of stability and comfort as well as satisfactory load transmission and mobility control.

SUMMARY OF THE INVENTION

The instant invention is an adjustable prosthetic socket. The adjustable prosthetic socket of the instant invention includes a cup, a lateral wall, and a brim. The cup includes a lateral cutaway portion, a lower closed portion, and an upper open portion. The brim is adapted for adjustable mounting in said cup via said upper open portion while the lateral wall is adapted for adjustable mounting in said lateral cutaway.

BRIEF DESCRIPTION OF THE DRAWINGS

For the purpose of illustrating the invention, there is shown in the drawings a form that is presently preferred; it being understood, however, that this invention is not limited to the precise arrangements and instrumentalities shown.

DETAILED DESCRIPTION OF THE INVENTION

Referring to the drawings wherein like numerals indicate like elements, there is shown, in FIGS. 1–4, a preferred embodiment of an adjustable prosthetic socket 10. The adjustable prosthetic socket 10 includes three fundamental components, namely, a cup 12, a lateral wall 14, and a brim 16. The adjustable prosthetic socket 10 may also include a locking mechanism 18. As will be appreciated, these components are mounted and combined into a single adjustable prosthetic socket 10 for mounting prosthesis, e.g. an artificial leg, to the above-knee residuum of a transfemoral amputee.

Figure 1:
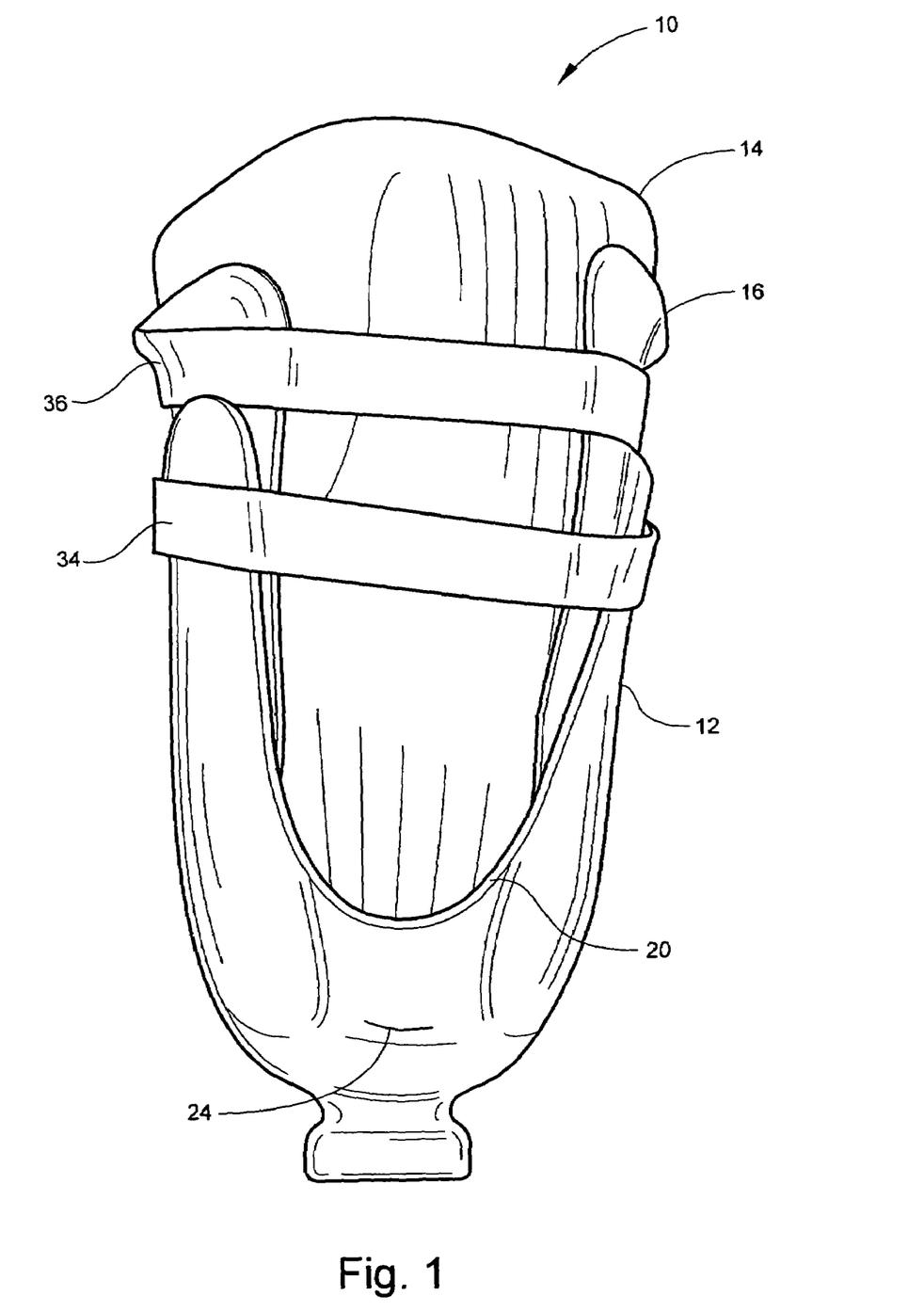
FIG. 1 is an elevational view of the lateral side of the instant invention.
Figure 2:
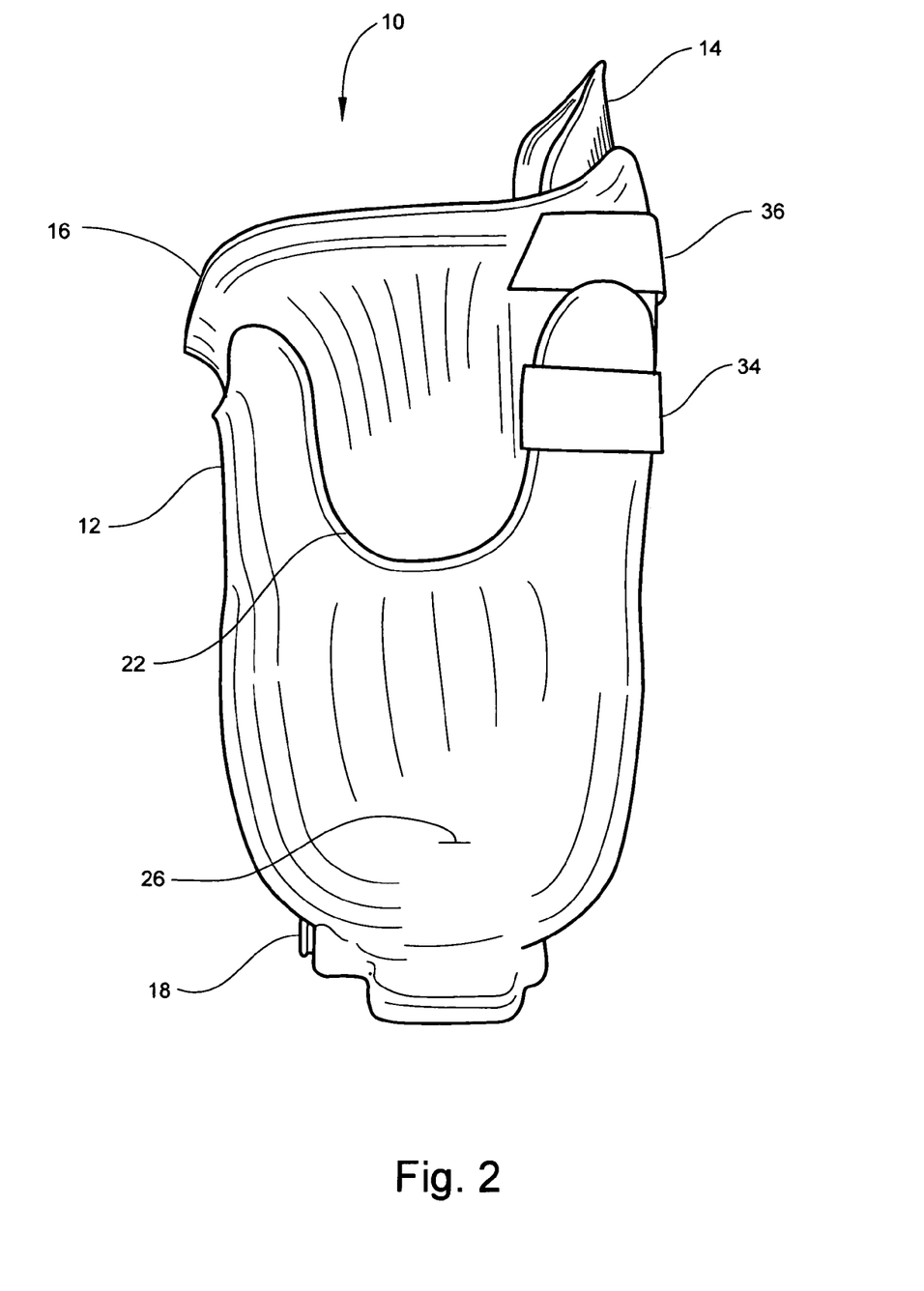
FIG. 2 is an elevational view of the posterior side of the instant invention.
Figure 3:
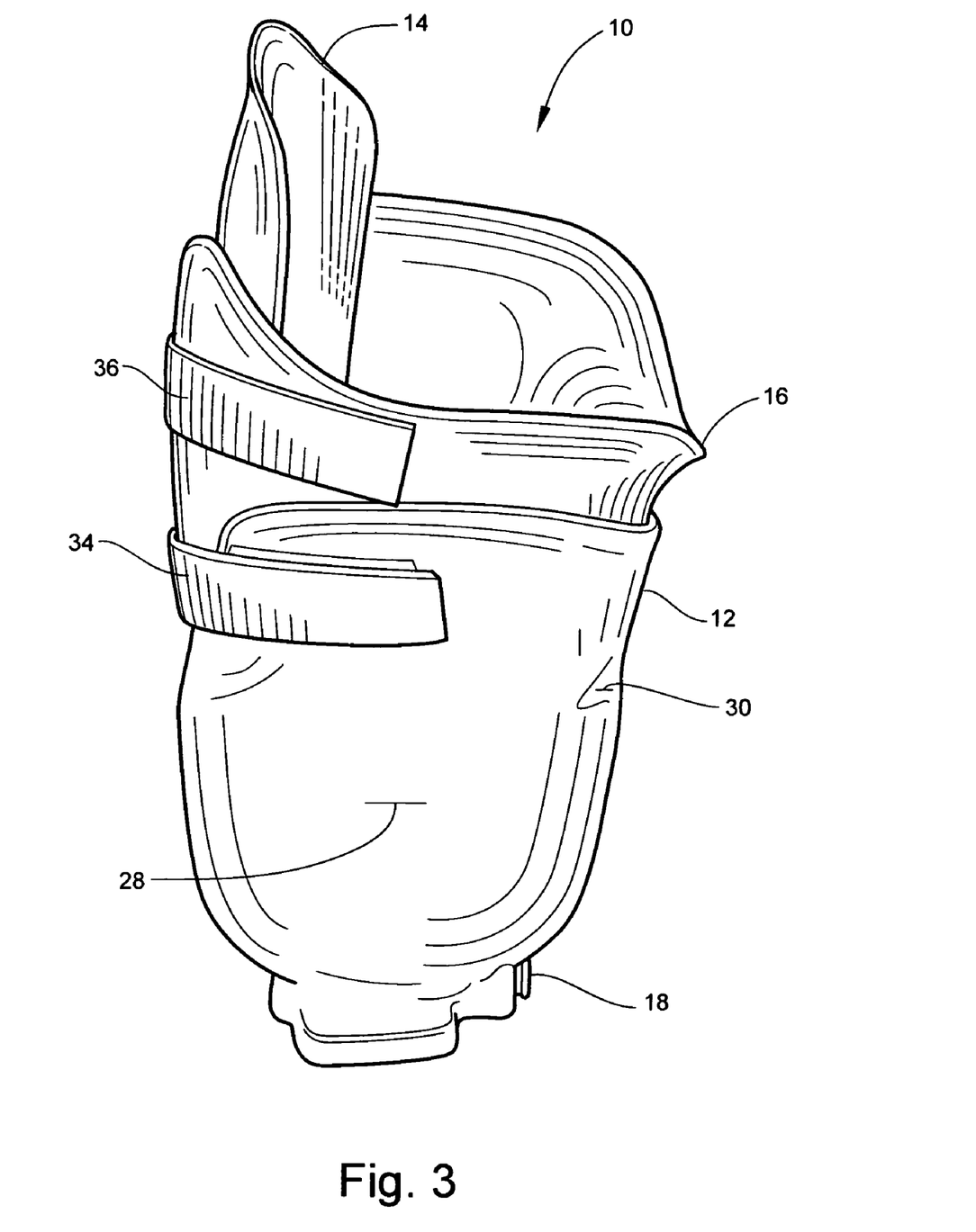
FIG. 3 is a perspective view of the anterior/medial of the instant invention.
Figure 4:
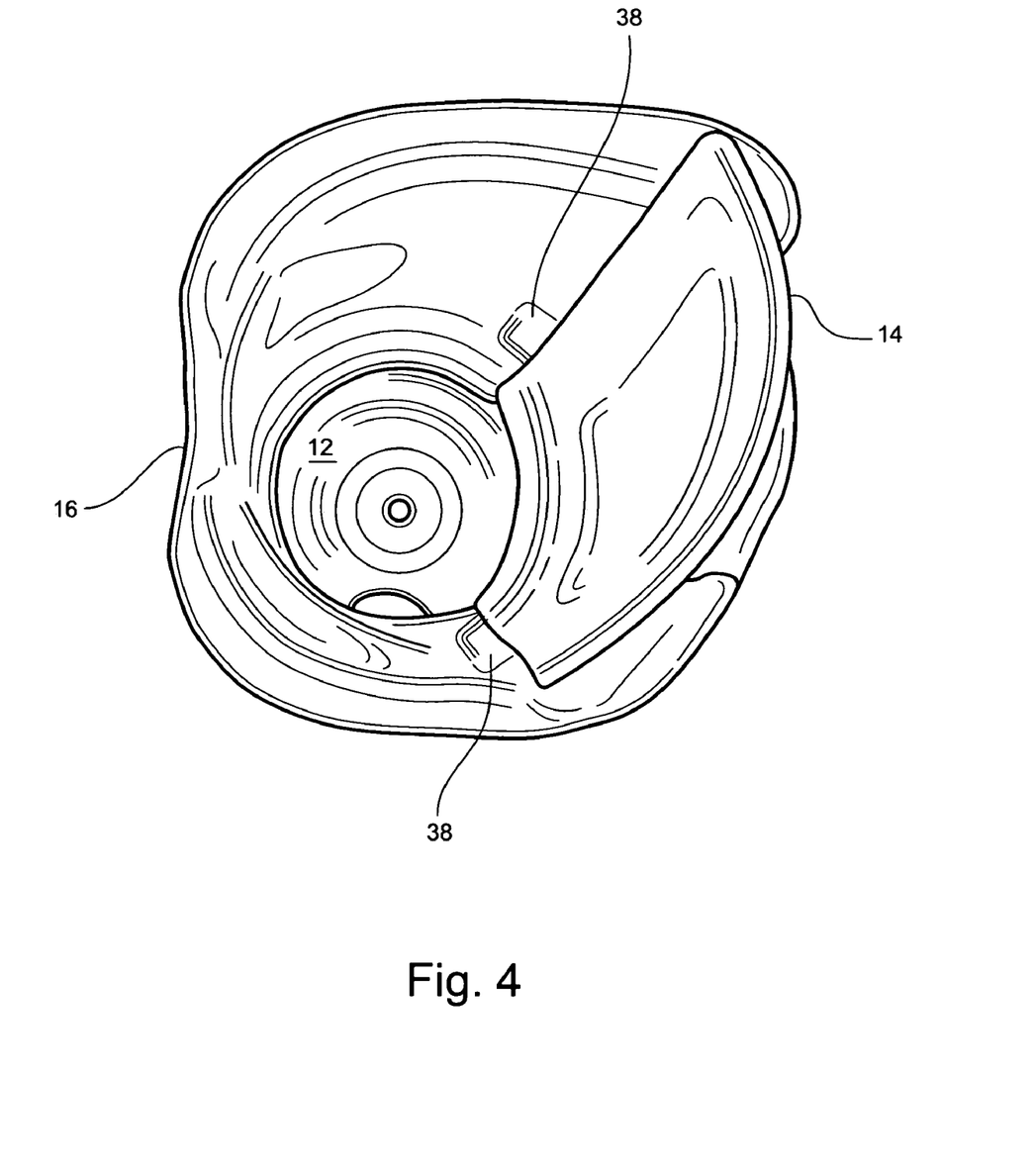
FIG. 4 is a top view of the instant invention.
Figure 5:
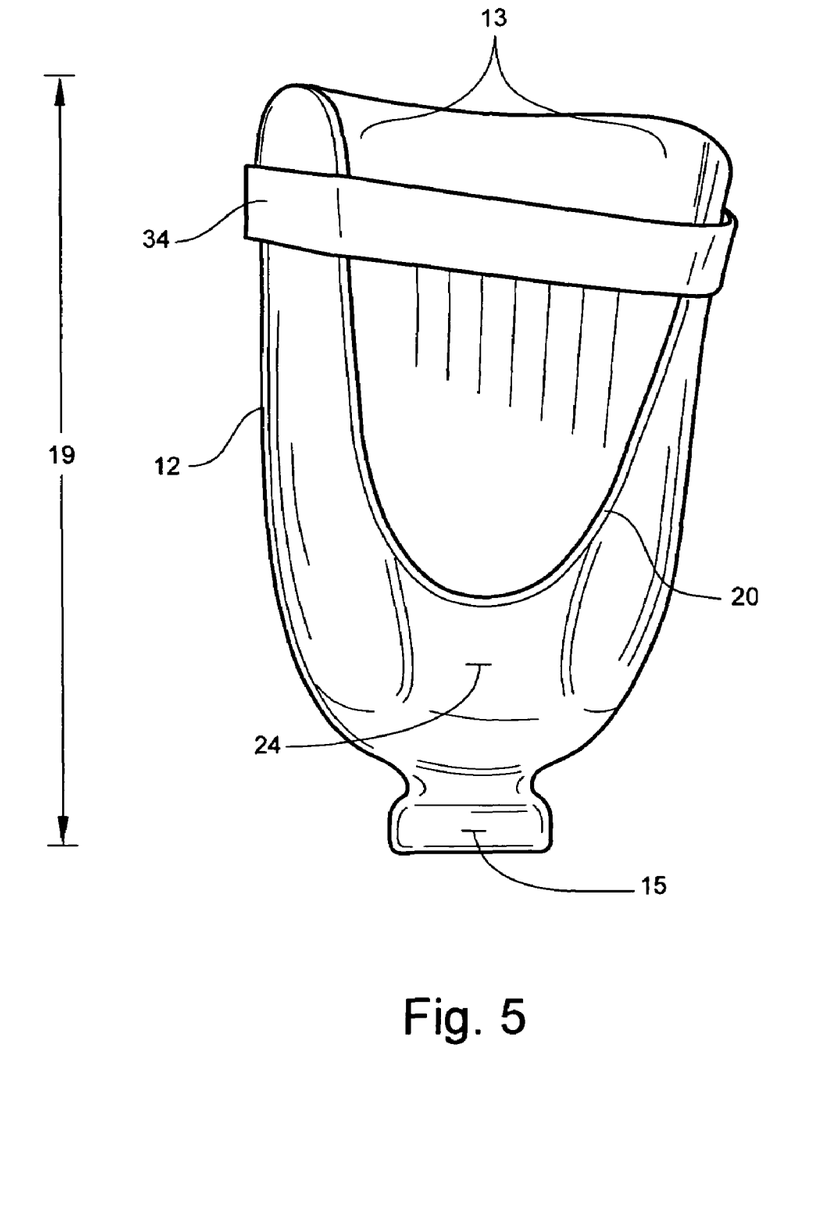
FIG. 5 is an elevational view of the lateral side of a cup.

Referring to FIGS. 1–5, in general cup 12 has four sides including lateral side 24, posterior side 26, anterior side 28, and medial side 30. Cup 12, as shown in FIG. 5, includes a lateral cutaway portion 20, a lower closed portion 15, and an upper open portion 13. Preferably, cup 12 also includes a posterior cutaway portion 22, as shown in FIG. 2. Cup 12 may have any shape; preferably, cup 12 has a shape suitable to adjustably receive and mount brim 16. More preferably, cup 12 has a generally arcuate contour in a vertical plane, and it is also of arcuate configuration, as viewed in cross section, as it extends in a horizontal plane. Cup 12 may be made of any material; preferably, cup 12 is made of polyolefin. More preferably, cup 12 is made of polypropylene. Cup 12 may have any vertical length 19; preferably, cup 12 has a vertical length 19 suitable to accommodate the length of the residuum of a transfemoral amputee. More preferably, cup 12 has vertical length in the range of 5 to 80 centimeter. Cup 12 may include the means for selective adjustment of the upper open portion 13. Means for selective adjustment of the upper open portion 13 include, but are not limited to, adjustable constricting means such as hooks and loops fastener devices, straps, tapes, cinches, screws, interlocking mechanisms, and combinations thereof. Preferably, cup 12 includes a hook and loop fastening device 34 as the constricting means for selective adjustment of the upper open portion 13.

The lateral cutaway portion 20 may occupy any region of cup 12; preferably, lateral cutaway portion 20 occupies the upper portion of the lateral side 24 of cup 12. The lateral cutaway portion 20 may have any shape or any size; preferably, lateral cutaway portion 20 has a complimentary shape and size to the lateral wall 14, as described in further detail hereinbelow. More preferably, the lateral cutaway portion 20 is adapted to facilitate both selective longitudinal adjustment and selective circumferential adjustment in socket 10. Most preferably, the lateral cutaway portion 20 is adapted to facilitate a selective longitudinal adjustment in the range of 0 to 3 centimeter upwardly or downwardly, and a selective circumferential adjustment of about 0 to 5 centimeter inwardly or outwardly in socket 10. Lateral cutaway portion 20 may have any length or width. Preferably, lateral cutaway has a length in the range of 5 to 100 centimeter, and a width in the range of 5 to 100 centimeter.

The lower closed portion 15 may have any shape or any size; preferably, lower closed portion 15 has a shape and a size suitable to receive the locking mechanism 18 and to provide total surface bearing capability of the residuum.

The upper open portion 13 may have any shape or any size. Preferably, upper open portion 13 has a shape and a size suitable to receive the brim 16, as described hereinbelow. More preferably, upper open portion 13 has a diameter in the range of 2 to 100 centimeter. Upper open portion 13 may be constricted or expanded any amount allowed by the inherent flexibility of the material of which it is made. Preferably, upper portion 13 may be constricted or expanded from about 0 to 5 centimeter. In addition, upper open portion 13 is adapted to facilitate both selective circumferential adjustment and selective longitudinal adjustment in socket 10. Preferably, the upper open portion 13 is adapted to facilitate a selective longitudinal adjustment of about 0 to 3 centimeter downwardly or upwardly, and a selective circumferential adjustment of about 0 to 5 centimeter inwardly or outwardly in socket 10.

Figure 6:
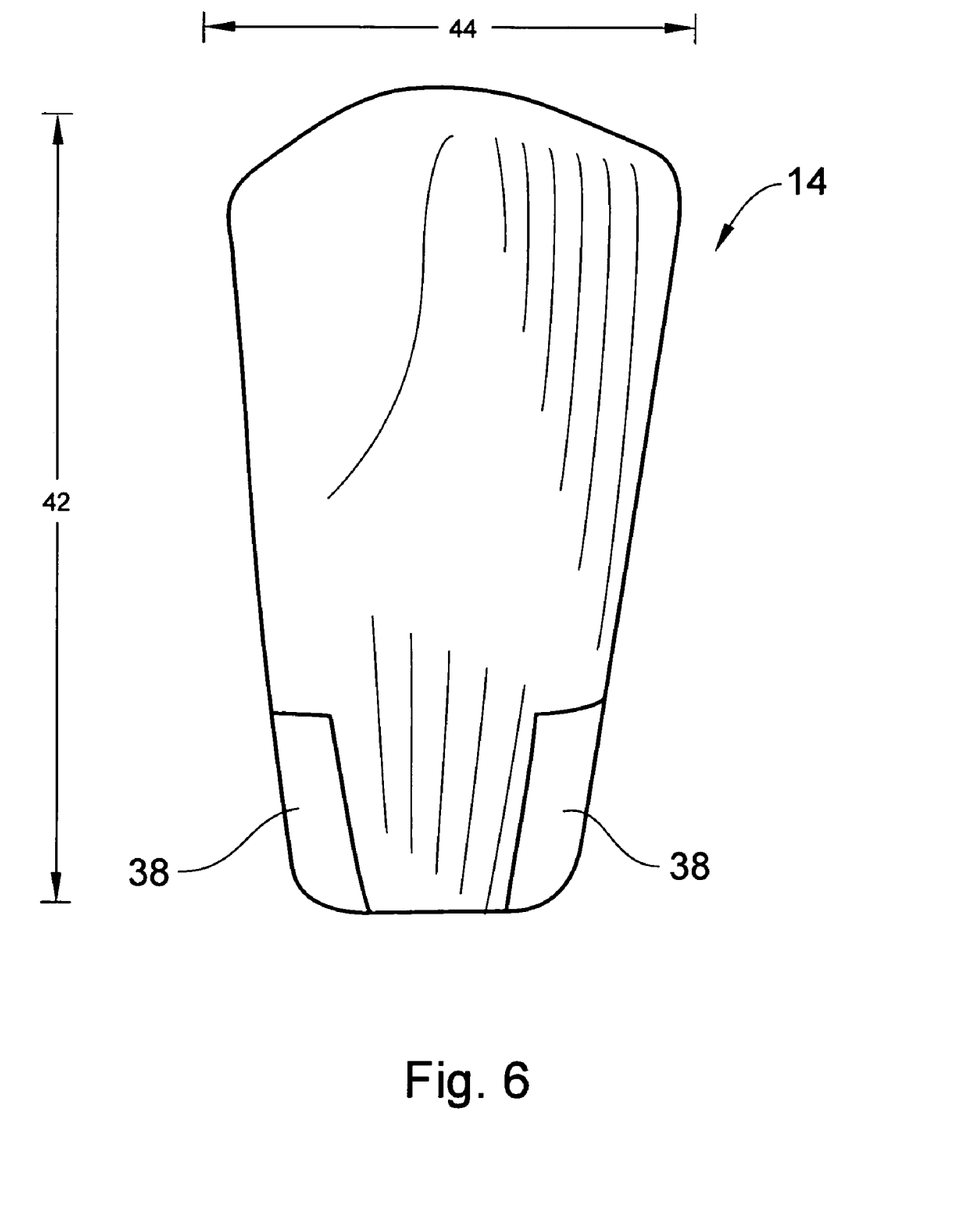
FIG. 6 is an elevational view of the front side of a lateral wall.

Referring to FIG. 6, lateral wall 14 may have any shape or size. Preferably, lateral wall 14 has a complementary shape and a size to the lateral cutaway 20. More preferably, lateral wall 14 has a generally arcuate contour as it extends upwardly, and it also is of arcuate configuration, as viewed in cross section, as it extends in a horizontal plane. The upper portion of the lateral wall 14 may be flared; and preferably, the upper portion of the lateral wall 14 is flared out. Lateral wall 14 may have any length 42 or any width 44. Preferably, lateral wall 14 has a length 42 approximately equal to a measurement from just proximal to the distal end of the residuum of an amputee to a selective point proximal to the greater trochanter, and a width 44 approximately equal to the diameter between the intersecting posterior-lateral and anterior-lateral brim sections, which depends on the approximate measure of the anterior-posterior diameter of the residuum of an amputee. More preferably, lateral wall 14 has a length 42 in the range of 5 to 100 centimeter, and a width 44 in the range of 5 to 100 centimeter. Lateral wall 14 may be made of any material. Preferably, lateral wall 14 is made of polyolefin, and more preferably, lateral wall 14 is made of polyethylene. In addition, preferably, lateral wall 14 is adapted to facilitate both selective longitudinal adjustment and selective circumferential adjustment in socket 10. More preferably, the lateral wall 14 is adapted to facilitate a selective longitudinal adjustment of about 0 to 3 centimeter downwardly or upwardly, and a selective circumferential adjustment of about 0 to 5 centimeter inwardly or outwardly in socket 10. Lateral wall 14 may include the means for adjustable mounting 38 into the lateral cutaway portion of Cup 12. Means for adjustable mounting 38 include, but are not limited to, adjustable fastener devices such as hooks and loops fastener devices, straps, tapes, cinches, screws, interlocking mechanisms, and combinations thereof.

Figure 7:
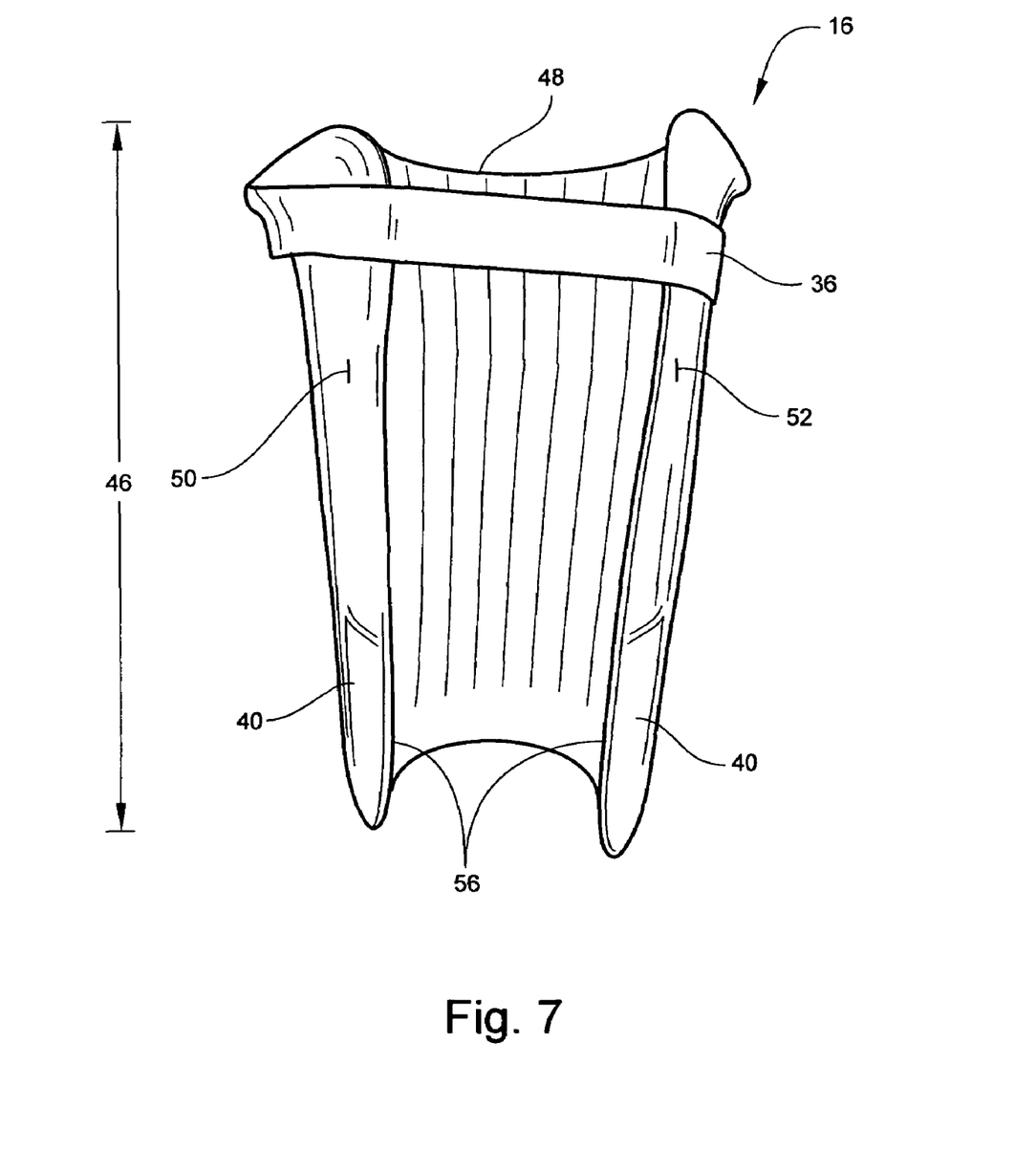
FIG. 7 is an elevational view of the lateral side of a brim.

Referring to FIG. 7, brim 16, as used herein, refers to a tubular shape sleeve comprising a medial section 48, a posterior section 50, an anterior section 52, and a lateral section 54 having a lateral cutaway segment 56. Preferably, brim 16 has a generally arcuate contour as it extends upwardly, and it also is of arcuate configuration, as viewed in cross section, as it extends in a horizontal plane. More preferably, brim 16 is adapted to adjustably receive the residuum of an amputee; thus, brim 16 is configured to conform to the anatomical contours of the residuum of the amputee as well as the intact skeletal structure of the amputee. Upper portion of brim 16 may be flared; and preferably, upper portion of brim 16 is flared out. Brim 16 may have any length 46 or any diameter; and preferably, brim 16 has a length 46 and a diameter suitable to accommodate the appropriate measured dimensions of the residuum of an amputee. More preferably brim 16 has a length 46 in the range of 5 to 100 centimeter, and a diameter in the range of 5 to 100 centimeter. Brim 16 may be made of any material; and preferably, brim 16 is made of a polyolefin; and more preferably, brim 16 is made of polyethylene. In addition, brim 16 is adapted to facilitate both selective longitudinal adjustment and selective circumferential adjustment in socket 10. More preferably, brim 16 is adapted to facilitate a selective longitudinal adjustment of about 0 to 3 centimeter downwardly or upwardly, and a selective circumferential adjustment of about 0 to 5 centimeter inwardly or outwardly in socket 10. Brim 16 may include the means for selective adjustment of its diameter.

Means for selective adjustment of the diameter of brim 16 include, but are not limited to, adjustable constricting devices such as hook and loop fastener devices, straps, tapes, cinches, screws, interlocking mechanisms, and combinations thereof. Preferably, means for selective adjustment of the diameter of the brim 16 is a hook and loop fastener device. Additionally, brim 16 may include the means for adjustable mounting 40 into the cup 12. Means for adjustable mounting 40 include, but are not limited to, adjustable fastener devices such as hooks and loops fastener devices, straps, tapes, cinches, screws, interlocking mechanisms, and combinations thereof.

In the manufacturing of socket 10, a replica of the residuum of an amputee is formed via the conventional molding methods. In the alternative, a replica of the residuum of an amputee is formed via custom rectification of a blank or existing mold using approximate circumferential, length, diameter, skeletal, and angular measurements. Preferably, the replica has four sides including a posterior side, an anterior side, a lateral side, and a medial side. Next, the replica is positioned horizontally so that the lateral side of the replica is facing upwardly. A material suitable for the formation of the lateral wall 14, e.g. polyethylene, is heated till malleable, then draped over the lateral side of the replica, stored under vacuum, and allowed to solidify to form the lateral wall 14. Subsequently, lateral wall 14 is removed from the replica, and preferably, lateral wall 14 is trimmed to conform to a shape or a size as described hereinabove. Then, using the same replica, a material suitable for the formation of the brim 16, e.g. polyethylene, is heated till malleable, then draped over the replica with the lateral wall 14 in place, stored under vacuum, and allowed to solidify to form the brim 16. Subsequently, brim 16 is removed from the replica, and preferably, brim 16 is trimmed to conform to a shape or a size as described hereinabove. Next, using the same replica, a material suitable for the formation of the cup 12, i.e. polypropylene, is heated till malleable, then draped over the replica with the lateral wall 14 and brim 16 in place, stored under vacuum, and allowed to solidify to form cup 12. Subsequently, cup 12 is removed from the replica, and preferably, cup 12 is trimmed to conform a shape or a size as described hereinabove. Next, adjustable constricting means 34 and 35, and adjustable mounting devices 38 and 40 are incorporated into the cup 12, the brim 16, and the lateral wall 14. Finally, locking mechanism 18 is integrated into cup 12 via appropriate fastening means.

Figure 8:
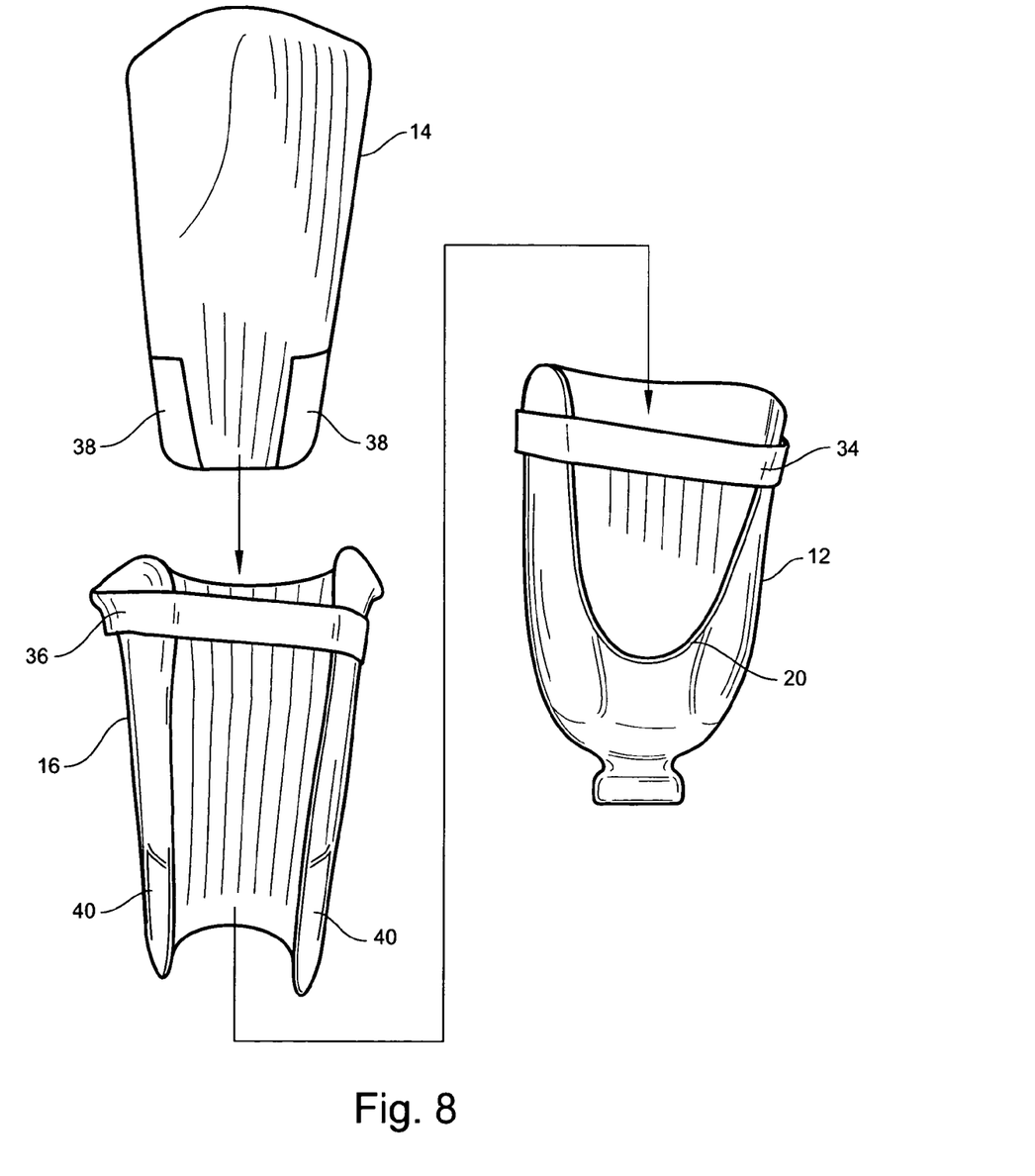
FIG. 8 is a first exploded view of the instant invention schematically illustrating how the adjustable prosthetic socket of the instant invention is being assembled.
Figure 9:
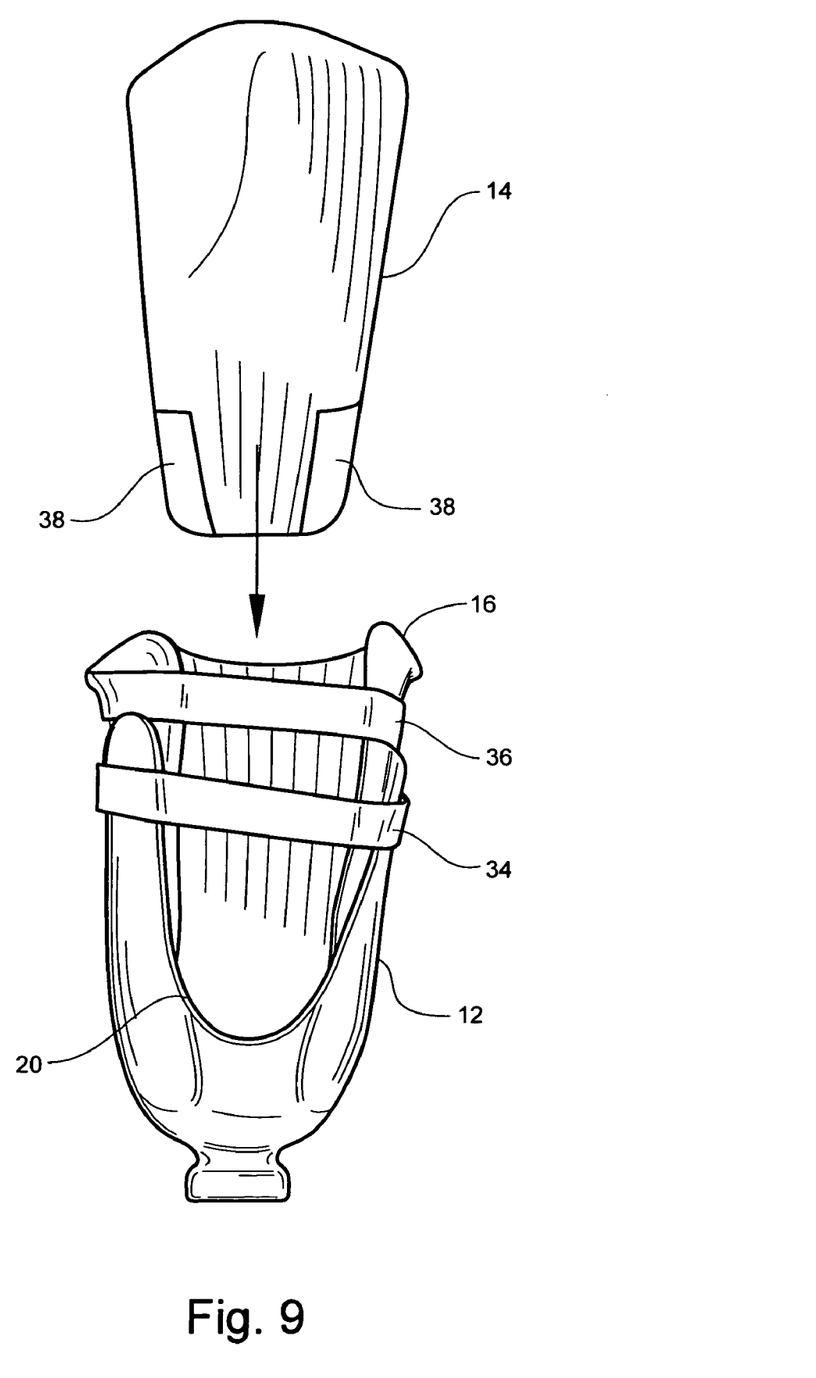
FIG. 9 is a second exploded view of the instant invention schematically illustrating how the adjustable prosthetic socket of the instant invention is being assembled.
Figure 10:
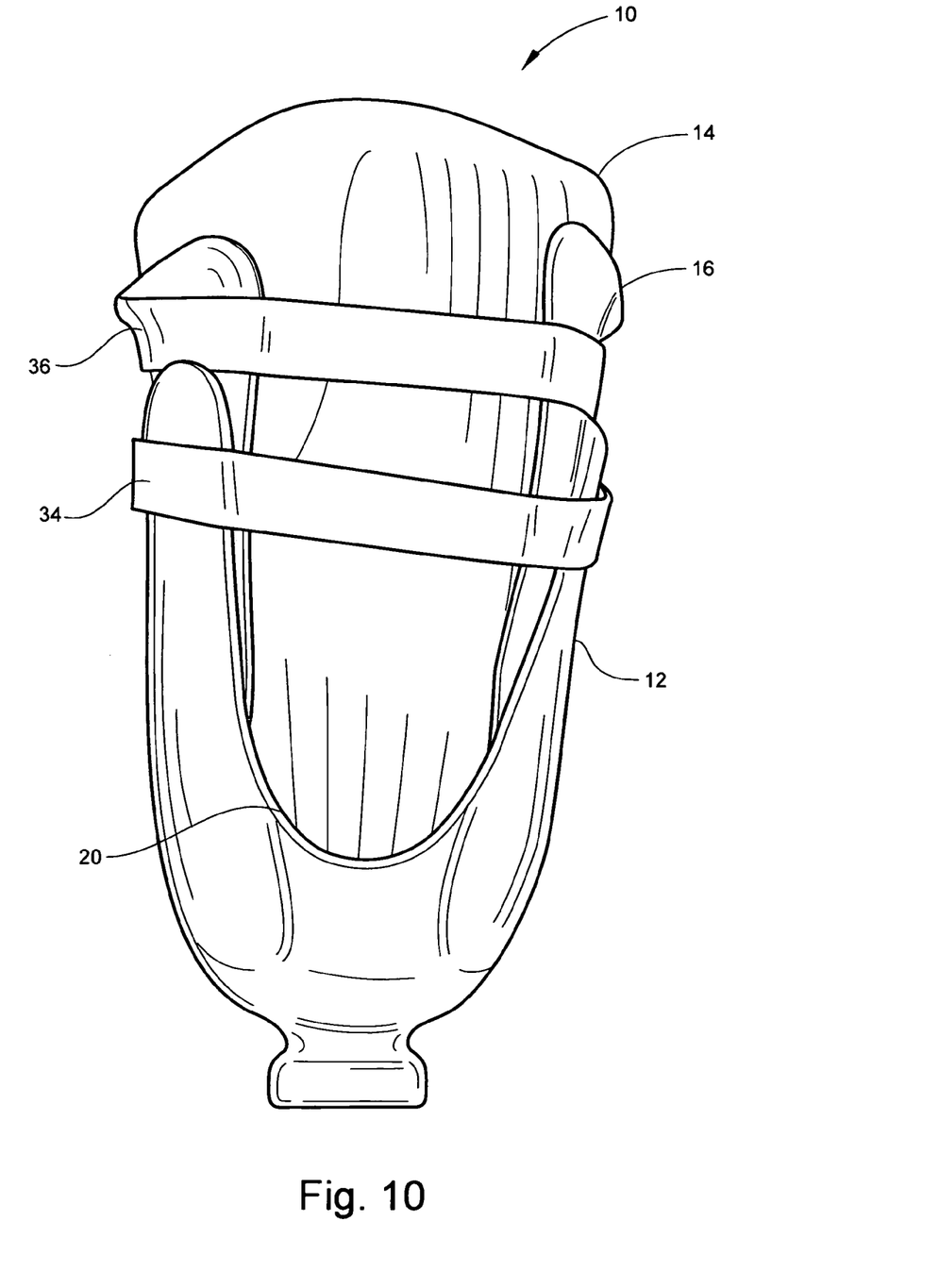
FIG. 10 is an elevational view of the lateral side of an assembled adjustable prosthetic socket of the instant invention.

In operation, referring to FIGS. 8–10, brim 16 is inserted into the cup 12 through the upper opening portion 13, and mounted thereto cup 12 via an adjustable mounting device 40, e.g. hooks and loops fastening device. Next, lateral wall 14 is mounted in the lateral cutaway portion of cup 12 via an adjustable mounting device 38, e.g. hooks and loops fastening device to form the adjustable prosthetic socket 10.

In preferred operation, a prosthetic leg (not shown) may include the adjustable socket 10 of the instant invention, a knee system (not shown), a shank system (not shown), and a foot-ankle system (not shown). Accordingly, such a prosthetic leg (not shown) including the adjustable socket 10 of the instant invention will provide a transfemoral amputee an easy fitting process while further providing a high level of stability and control as well as satisfactory load transmission and comfort.

The present invention may be embodied in other forms without departing from the spirit and the essential attributes thereof, and, accordingly, reference should be made to the appended claims, rather than to the foregoing specification, as indicating the scope of the invention.

I claim:

1. An adjustable prosthetic socket comprising:
   a cup having a lateral cutaway portion, a lower closed portion, and an upper open portion;
   a brim, said brim being a tubular shape sleeve having a lower open end, an upper open end, and a lateral cutaway segment extending from said upper open end to said lower open end, wherein said brim being adapted for adjustable mounting in said cup via said upper open portion; and
   a lateral wall adapted for adjustable mounting in said lateral cutaway portion.

2. The adjustable prosthetic socket according to claim 1, wherein said socket being adapted for both longitudinal adjusting and circumferential adjusting.

3. The adjustable prosthetic socket according to claim 1, wherein said socket being adapted for a longitudinal adjusting in the range of 0 to 3 centimeter downwardly or upwardly.

4. The adjustable prosthetic socket according to claim 1, wherein said socket being adapted for a circumferential adjusting in the range of 0 to 5 centimeter inwardly or outwardly.

5. The adjustable prosthetic socket according to claim 1, wherein said cup being adapted for circumferential adjusting.

6. The adjustable prosthetic socket according to claim 1, wherein said lateral wall being adapted for longitudinal adjusting.

7. The adjustable prosthetic socket according to claim 1, wherein said brim being adapted for circumferential adjusting.

8. The adjustable prosthetic socket according to claim 1, wherein said adjustable prosthetic socket further including an adjustable constricting device selected from the group consisting of hooks and loops fastener devices, straps, tapes, cinches, screws, interlocking mechanisms, and combinations thereof.

9. The adjustable prosthetic socket according to claim 1, wherein said upper open end of said brim being flared outwardly.

10. The adjustable prosthetic socket according to claim 1, wherein said lateral wall having an upper end, said upper end being flared outwardly.

11. The adjustable prosthetic socket according to claim 1, wherein said socket further including a locking mechanism.

12. The adjustable prosthetic socket according to claim 1, wherein said cup being polyolefin.

13. The adjustable prosthetic socket according to claim 12, wherein polyolefin being polypropylene.

14. The adjustable prosthetic socket according to claim 1, wherein said lateral wall being polyolefin.

15. The adjustable prosthetic socket according to claim 14, wherein polyolefin being polyethylene.

16. The adjustable prosthetic socket according to claim 1, wherein said brim being polyolefin.

17. The adjustable prosthetic socket according to claim 16, wherein polyolefin being polyethylene.

18. A prosthetic leg comprising:
   an adjustable prosthetic socket comprising:
      a cup having a lateral cutaway portion, a lower closed portion, and an upper open portion;
      a brim, said brim, being a tubular shape sleeve having a lower open end, an upper open end, and a lateral cutaway sequent extending from said upper open end to said lower open end, wherein said brim being adapted for adjustable mounting in said cup via said upper open portion; and a lateral wall adapted for adjustable mounting in said lateral cutaway portion.

19. A method of making an adjustable prosthetic socket comprising:

providing a cup having a lateral cutaway portion, a lower closed portion, and an upper open portion;

providing a brim, said brim being a tubular shape sleeve having a lower open end, an upper open end, and a lateral cutaway segment extending from said upper open end to said lower open end, wherein said brim being adapted for adjustable mounting in said cup via said upper open portion;

providing a lateral wall adapted for adjustable mounting in said lateral cutaway portion;

mounting said brim into said cup via said upper portion; and mounting said lateral wall into said lateral cutaway portion.

* * * * *